United States Patent [19]

Stroppolo et al.

[11] Patent Number: 5,488,069
[45] Date of Patent: Jan. 30, 1996

[54] OPHTHALMIC PHARMACEUTICAL COMPOSITION CONTAINING N-ACETYL-CYSTEINE AND POLYVINYLALCOHOL

[75] Inventors: Federico Stroppolo, Pregassona, Switzerland; Daniele Bonadeo, Varese, Italy; Francesco Tocchini, Bissone, Switzerland; Annibale Gazzaniga, Rescaldina, Italy

[73] Assignee: Zambon Group S.p.A., Vicenza, Italy

[21] Appl. No.: 253,587

[22] Filed: Jun. 3, 1994

Related U.S. Application Data

[63] Continuation of Ser. No. 5,397, Jan. 15, 1993, abandoned.

[30] Foreign Application Priority Data

Jan. 16, 1992 [IT] Italy .................................. MI92A0074

[51] Int. Cl.⁶ .......................... A61K 31/195; A61K 31/74
[52] U.S. Cl. ........................ 514/772.4; 514/912; 514/913; 514/914; 514/915; 424/78.04
[58] Field of Search ................. 424/78.04, 427, 424/428; 514/772.4, 912, 913, 914, 95

[56] References Cited

U.S. PATENT DOCUMENTS

| | | | |
|---|---|---|---|
| 4,120,949 | 10/1978 | Bapatla et al. | 424/78.04 |
| 4,131,651 | 12/1978 | Shah et al. | 424/78.04 |
| 4,409,205 | 10/1983 | Shively | 424/78.04 |
| 4,883,658 | 11/1984 | Holly | 424/78.04 |

FOREIGN PATENT DOCUMENTS

| | | |
|---|---|---|
| 901885 | 7/1985 | Belgium . |
| 0499882 | 8/1992 | Italy . |
| WO-A-9221049 | 11/1992 | WIPO . |

OTHER PUBLICATIONS

Acta Ophthamol., vol. 55, No. 1, 1977, pp. 23–034, M. S. Norn 'Effects of ophthalmic vehicles on the stability of the precorneal film'.
Curr. Ther. vol. 28, No. 9, 1987, pp. 99–108, T. R. Ellingham 'The dry eye. Modern management'.
Patent Abstracts of Japan, vol. 8, No. 114 (C–225) 1984 of JP-A-59 028 498 (Yatoron).
Drug Ther. Bull., vol. 23, No. 21, 1985, pp. 81–82, 'Management of the dry eye'.
The Merck Index—XI Ed.—No. 7562, p. 1208, "Polyvinyl Alcohol".
The Merck Index—XI Ed., No. 82, p. 14, "Acetylcysteine".
Opthalmic Drug Delivery, Biopharmaceutical, Technological and Clinical Aspects, vol. 11, (1987), M. S. Saettone, et al., pp. 37–47, "Semiology Of The Tear Film."

Primary Examiner—Carlos A. Azpuru
Attorney, Agent, or Firm—Oblon, Spivak, McClelland, Maier, & Neustadt

[57] ABSTRACT

An ophthalmic pharmaceutical composition containing an association of N-acetyl-cysteine and polyvinylalcohol useful for the treatment of keratoconjunctivitis sicca.

7 Claims, No Drawings

OPHTHALMIC PHARMACEUTICAL COMPOSITION CONTAINING N-ACETYL-CYSTEINE AND POLYVINYLALCOHOL

This application is a continuation of application Ser. No. 08/005,397, filed on Jan. 5, 1993, now abandoned.

The present invention relates to a pharmaceutical composition for ophthalmic use and, more particularly, it relates to a pharmaceutical composition useful for the treatment of keratoconjunctivitis sicca containing an association of N-acetyl-cysteine and polyvinylalcohol.

Keratoconjunctivitis sicca, commonly known as dry-eye syndrome, is an ophthalmic disorder characterized by a reduced production of lachrymal secretion and by an alteration of the composition of the tear film.

These alterations are responsible of the corneal dryness with consequent hyperaemia, pain, itching, burning and foreign body sensation. The simplest therapeutic approach in the treatment of keratoconjunctivitis sicca is that of using the so-called artificial tears that is solutions of polymers which are able to increase the thickness of the tear film and to retain a larger amount of liquid in the eye.

Polyvinylalcohol (The Merck Index—XI Ed.— No. 7562, page 1208), hereinafter indicated as PVA, is a synthetic polymer widely used for the preparation of artificial tears.

The use of artificial tears affects and solves only some of the problems related to keratoconjunctivitis sicca and specifically those due to the mechanical consequences of the reduced moistening and lubricating capacity of the tear film.

N-acetyl-cysteine (The Merck Index, XI Ed., No. 82, page 14), hereinafter indicated as NAC, is a known mucolytic drug already used also in ophthalmic therapy in the treatment of keratoconjunctivitis sicca for its ability to interact with the mucoproteins and, therefore, to decrease the viscosity of the tear film.

PVA and NAC act on the symptoms of keratoconjunctivitis sicca with two completely different mechanisms of action, that is the increase of the thickness of the tear film due to the sticking properties and the decrease of the viscosity of the tear film due to the mucolytic properties, respectively.

We have now surprisingly found that the association of NAC and PVA in the treatment of keratoconjunctivitis sicca produces a significant improvement of the symptoms of the disease not only with respect to the efficacy but also with regard to the onset of the effect in comparison with the treatment with the single components of the association.

Therefore, it is an object of the present invention an ophthalmic pharmaceutical composition containing an association of NAC and PVA as active ingredient.

The pharmaceutical composition object of the invention is useful in the treatment of keratoconjunctivitis sicca.

The concentration of NAC in the composition object of the invention is generally between 3% and 5% weight/volume.

The concentration of PVA in the composition object of the invention is generally between 1% and 97% weight/volume.

The composition object of the invention can be formulated in a liquid pharmaceutical preparation such as eye-drops or in a solid pharmaceutical preparation such as ocular inserts, It is clear that the concentration of PVA in the composition of the invention will vary depending on the pharmaceutical preparation. In particular, the concentration of PVA will be preferably between 3% and 7% weight/volume in eye-drops and between 10% and 97% weight/volume in inserts.

Preferably, NAC and PVA are used in the same weight/volume concentration.

More preferably, concentrations of NAC and PVA amounting to 4% weight/volume are used.

The compositions of the invention can further contain pharmaceutical excipients suitable for the preparation of ophthalmic formulations. Examples of such excipients are preserving agents, buffering agents, chelating agents, antioxidant agents and salts for regulating the osmotic pressure.

The preparation of the pharmaceutical compositions object of the invention is carried out according to conventional techniques.

According to the general practice about compositions for ophthalmic use, the compositions of the invention have to be sterilized. The procedure can be accomplished by known techniques like sterilizing filtration of the solution or by heating of the solution in the ampoule ready for use.

As above reported, the NAC-PVA association produces a significant improvement of the symptoms of keratoconjunctivitis sicca not only with regard to the efficacy but also with regard to the onset of the effect in comparison with the treatment with NAC alone or with PVA alone.

In fact, the composition object of the invention was compared with similar compositions containing the same amounts of PVA only or of NAC only, respectively (see example 5).

The efficacy of the NAC-PVA association with respect to the single components was determined by the evaluation of the Schirmer test, of the break-up time (BUT) and of the ocular dryness.

For a reference to the tests which were used for the evaluation of the efficacy of the NAC-PVA association see M. Rolando, "Semiology of the tear film"—Ophthalmic Drug Delivery, Biopharmaceutical, Technological and Clinical Aspects—M. S. Saettone, G. Bucci, P. Speiser (eds) Fidia Research Series, vol. 11, Liviana Press, Padova, (1987).

It is evident from the results of the comparison how the improvement of the monitored parameters is significantly greater after treatment with the NAC-PVA association that with the single components but, most of all, it is already significantly greater since the first week of treatment.

It is worth underlining the therapeutic importance of the improvements of the symptoms of keratoconjunctivitis sicca observed during the treatment with the NAC-PVA association.

In fact, in addition to the self-evident advantage of a significantly earlier onset of the efficacy of the treatment, the use of the NAC-PVA association allows also to lower the therapeutically effective doses of each active ingredient.

The composition object of the invention showed to have greater and more rapid efficacy also with respect to ophthalmic pharmaceutical compositions containing a higher concentration of NAC (see example 6).

The composition of the invention, moreover, resulted to be endowed with a good compliance by the patients.

In order to better illustrate the present invention the following examples are now given.

EXAMPLE 1

Eye-drops containing NAC (4%) and PVA (4%)

In a beaker, PVA 25000 (760 g) was added to deionized water (10 l) under vigorous stirring.

The solution was kept under stirring for some minutes, heated to 90° C. and kept under these conditions for 10 minutes.

The solution was left to cool up to room temperature (solution A). In a second beaker, sodium hydroxide (201.4 g) was dissolved in deionized water (1.5 l) (solution B).

In another beaker, benzalkonium chloride (0.95 g), disodium edetate (19 g), sodium chloride (127.3 g) and potassium chloride (28.5 g) were dissolved in deionized water (5 l).

After insertion of a nitrogen bubbler, NAC (760 g) was suspended into the solution under stirring.

Solution B was added to the resulting suspension up to obtain a final pH of about 6.0.

The resultant solution was poured into solution A under nitrogen flow and the resulting solution was kept under stirring and nitrogen flow for 10 minutes. The pH was checked and in case corrected to about 6.0.

Deionized water was added up to the final volume (19 l) and the solution was heated at 70° C. under mild stirring and nitrogen flow.

The solution was filtered at 70° C., left to cool to 50° C. and distributed into vials under nitrogen flow.

Each vial contained 10 ml of eye-drops having the following percent composition (weight/volume):

NAC 4.0%
PVA 4.0%
Disodium edetate 0.1%
Sodium chloride 0.67%
Potassium chloride 0.15%
Benzalkonium chloride 0.005%
Sodium hydroxide q.s. to pH 6.0 water q.s. to 10 ml.

EXAMPLE 2

Eye-drops Containing NAC (4%) and PVA (6.6%)

In a beaker, PVA 15000 (1254 g) was added to deionized water (10 l) under vigorous stirring.

The solution was kept under stirring for some minutes, heated to 90° C. and kept under these conditions for 10 minutes.

The solution was left to cool up to room temperature (solution A).

In a second beaker, sodium hydroxide (201.4 g) was dissolved in deionized water (1.5 l) (solution B).

In another beaker, benzalkonium chloride (0.95 g), edetate disodium (19 g), sodium chloride (127.3 g) and potassium chloride (28.5 g) were dissolved in deionized water (5 l).

After introduction of a nitrogen bubbler, NAC (760 g) was suspended into the solution under stirring.

Solution B was added to the suspension up to obtaining a final pH of about 6.0.

The resultant solution was poured into solution A under nitrogen flow and the solution was kept under stirring and nitrogen flow for 10 minutes. The pH was checked and in case corrected to about 6.0. Deionized water was added up to the final volume (19 l) and the solution was heated at 70° C. under mild stirring and nitrogen flow. The solution was filtered at 70° C., left to cool to 50° C. and distributed into vials under nitrogen flow.

Each vial contained 5 ml of eye-drops having the following percent composition (weight/volume):

NAC 4.0%
PVA 6.6%
Disodium edetate 0.1%
Sodium chloride 0.67%
Potassium chloride 0.15%
Benzalkonium chloride 0.005%
Sodium hydroxide q.s. to pH 6.0 water q.s. to 5 ml.

EXAMPLE 3

Comparative Eye-drops Containing NAC (4%)

In a beaker, sodium hydroxide (102 g) was dissolved in deionized water (1 l) under stirring (solution A).

In another beaker, disodium edetate (10 g), sodium chloride (67 g) and potassium chloride (15 g) were dissolved in deionized water (5 l).

A nitrogen bubbler was inserted into the resultant solution and NAC (400 g) was suspended under stirring.

Solution A up to pH 6.0 and, then, benzalkonium chloride (0.5 g) were added to the suspension.

The solution was brought up to the final volume (10 l) with deionized water and filtered through a 0.2 μ sterilizing membrane.

The solution was distributed into vials under nitrogen.

Each vial contained 5 ml of eye-drops having the following percent composition (weight/volume):

NAC 4.0%
Disodium edetate 0.1%
Sodium chloride 0.67%
Potassium chloride 0.15%
Benzalkonium chloride 0.005%
Sodium hydroxide q.s. to pH 6.0 water q.s. to 5 ml.

EXAMPLE 4

Comparative eye-drops Containing PVA (4%)

In a beaker, benzalkonium chloride (0.45 g), disodium edetate (9.0 g), sodium chloride (60.3 g) and potassium chloride (13.5 g) were dissolved in deionized water (4 l).

Under vigorous stirring, PVA 15000 (360 g) was added to the solution and the resultant solution was brought up to the final volume (9 l) with deionized water and the pH was corrected to 6.0 with sodium hydroxide.

The solution was heated to 90° C., kept at this temperature for at least 5 minutes and filtered. After cooling at 50° C., the solution was distributed into vials. Each vial contained 5 ml of eye-drops having the following percent composition (weight/volume):

PVA 4.0%
Disodium edetate 0.1%
Sodium chloride 0.67%
Potassium chloride 0.15%
Benzalkonium chloride 0.005%
Sodium hydroxide q.s. to pH 6.0 water q.s. to 5 ml.

EXAMPLE 5

Pharmaceutical activity of eye-drops containing NAC (4%) and PVA (4%) in comparison to eye-drops containing NAC (4%) and with eye-drops containing PVA (4%)

Eye-drops containing NAC (4%) and PVA (4%), hereinafter indicated as NAC-PVA eye-drops, eye-drops containing NAC (4%), hereinafter indicated as NAC eye-drops, and eye-drops containing PVA (4%), hereinafter indicated as PVA eye-drops, prepared as described in the previous example 1, 3 and 4 respectively, were administered to patients suffering from keratoconjunctivitis sicca for a period of 3 months at the dose of 1–2 drops/3–4 times a day.

The following efficacy parameters Schirmer test, break-up time (BUT) and ocular dryness were evaluated at the beginning of the treatment and after 1 week, 1 month, 2 months and 3 months.

The number of patients was 50, 50, 46, 44 and 43 for NAC-PVA eye-drops, 49, 49, 46, 43 and 42 for NAC eye-drops and 51, 50, 48, 47 and 46 for PVA eye-drops at the beginning of the treatment and after 1 week, 1 month, 2 months and 3 months respectively.

The obtained data are reported in table 1.

Table 1

Efficacy of NAC-PVA eye-drops, NAC eye-drops and PVA eye-drops expressed as Schirmer test, BUT and ocular dryness after 1 week, 1 month, 2 months and 3 months of treatment.

TABLE 1

Efficacy of NAC-PVA eye-drops, NAC eye-drops and PVA eye-drops expressed as Schirmer test, BUT and ocular dryness after 1 week, 1 month, 2 months and 3 months of treatment.

|  | Treatment time | NAC-PVA eye-drops | NAC eye-drops | PVA eye-drops |
|---|---|---|---|---|
| Schirmer test (mm) | initial | 4.74 ± 0.27 | 4.49 ± 0.27 | 4.49 ± 0.30 |
|  | 1 week | 8.52 ± 0.55 | 7.33 ± 0.56 | 6.18 ± 0.47 |
|  | 1 month | 10.94 ± 0.69 | 8.80 ± 0.67 | 7.60 ± 0.53 |
|  | 2 months | 11.25 ± 0.70 | 8.98 ± 0.71 | 7.68 ± 0.58 |
|  | 3 months | 11.95 ± 0.70 | 9.39 ± 0.76 | 8.09 ± 0.60 |
| BUT (sec.) | initial | 8.28 ± 0.38 | 7.56 ± 0.39 | 7.16 ± 0.38 |
|  | 1 week | 11.92 ± 0.58 | 9.83 ± 0.51 | 8.58 ± 0.62 |
|  | 1 month | 13.41 ± 0.80 | 11.39 ± 0.71 | 9.60 ± 0.69 |
|  | 2 months | 14.25 ± 0.84 | 12.19 ± 0.81 | 10.00 ± 0.76 |
|  | 3 months | 15.16 ± 0.89 | 12.68 ± 0.92 | 10.57 ± 0.81 |
| Ocular dryness | initial | 2.48 ± 0.15 | 2.43 ± 0.16 | 2.57 ± 0.16 |
|  | 1 week | 1.52 ± 0.15 | 1.65 ± 0.13 | 1.74 ± 0.16 |
|  | 1 month | 0.94 ± 0.14 | 1.20 ± 0.12 | 1.42 ± 0.16 |
|  | 2 months | 0.75 ± 0.13 | 1.05 ± 0.12 | 1.26 ± 0.13 |
|  | 3 months | 0.74 ± 0.12 | 0.98 ± 0.12 | 1.20 ± 0.14 |

The data reported in table 1 show how the improvement of the monitored parameters (Schirmer test, BUT and ocular dryness) was significantly greater after treatment with NAC-PVA eye-drops than after treatment with NAC eye-drops or PVA eye-drops.

In addition, this improvement was significantly greater since the first week of treatment.

A similar improvement was observed with respect to the total symptom score of keratoconjunctivitis sicca.

EXAMPLE 6

Pharmacological activity of eye-drops containing NAC (4%) and PVA (4%) in comparison to commercial eye-drops containing NAC (5%)

NAC-PVA eye-drops, prepared as described in example 1 and commercial eye-drops (Brunac® Trademark of Bruschettini S.r.l. Italy) having the following percent composition (weight/volume):

NAC 5%
Sodium phosphate dibasic 4%
Sodium bicarbonate 2.67%
Hydroxypropylmethylcellulose 0.35%
Benzalkonium chloride 0.02%
Sodium calcium edetate 0.005% water q.s. to 100 ml hereinafter indicated as eye-drops R, were administered to patients suffering from keratoconjunctivitis sicca for a period of 3 months at the dose of 1–2 drops/3–4 times a day.

The following efficacy parameters were monitored at the beginning of the treatment and after 1 week, 1 month, 2 months and 3 months: Schirmer test, break-up time (BUT) and ocular dryness.

The number of patients was 51, 50, 48, 46 and 34 for NAC-PVA eye-drops, 49, 48, 46, 40 and 37 for R eye-drops at the beginning of the treatment and after 1 week, 1 month, 2 months and 3 months respectively. The obtained data are reported in table 2.

TABLE 2

Efficacy of NAC-PVA eye-drops and R eye-drops expressed as Schirmer test, BUT and ocular dryness after 1 week, 1 month, 2 months and 3 months of treatment.

TABLE 2

Efficacy of NAC-PVA eye-drops and R eye-drops expressed as Schirmer test, BUT and ocular dryness after 1 week, 1 month, 2 months and 3 months of treatment.

|  | Treatment time | NAC-PVA eye-drops | R eye-drops |
|---|---|---|---|
| Schirmer test (mm) | initial | 3.60 ± 0.37 | 3.86 ± 0.32 |
|  | 1 week | 5.69 ± 0.57 | 4.80 ± 0.46 |
|  | 1 month | 7.75 ± 0.64 | 5.66 ± 0.51 |
|  | 2 months | 8.60 ± 0.67 | 6.48 ± 0.58 |
|  | 3 months | 8.93 ± 0.80 | 6.84 ± 0.64 |
| BUT (sec.) | initial | 5.95 ± 0.46 | 5.92 ± 0.36 |
|  | 1 week | 7.36 ± 0.52 | 6.48 ± 0.45 |
|  | 1 month | 8.75 ± 0.55 | 7.42 ± 0.52 |
|  | 2 months | 9.60 ± 0.59 | 8.04 ± 0.55 |
|  | 3 months | 10.27 ± 0.72 | 8.31 ± 0.65 |
| Ocular dryness | initial | 2.59 ± 0.14 | 2.43 ± 0.15 |
|  | 1 week | 1.64 ± 0.15 | 1.77 ± 0.15 |
|  | 1 month | 0.92 ± 0.14 | 1.37 ± 0.13 |
|  | 2 months | 0.78 ± 0.10 | 1.05 ± 0.14 |
|  | 3 months | 0.68 ± 0.13 | 0.76 ± 0.14 |

The data reported on table 2 show how the improvement of the monitored parameters (Schirmer test, BUT and ocular dryness) was significantly greater after treatment with NAC-PVA eye-drops than after treatment with R eye-drops containing a higher amount of NAC.

In addition, this improvement was significantly greater since the first week of treatment.

A similar improvement was observed with respect to the total symptom scope of kepatoconjunctivitis sicca.

What we claim is:

1. An ophthalmic pharmaceutical comprising 3–5% weight per volume of N-acetyl-cysteine, and 1–97% weight per volume polyvinylalcohol.

2. The ophthalmic pharmaceutical of claim 1, wherein said N-acetyl-cysteine and said polyvinylalcohol have equal weight per volume concentrations.

3. The ophthalmic pharmaceutical of claim 1, comprising 4% weight per volume N-acetyl-cysteine, and 4% weight per volume polyvinylalcohol.

4. The ophthalmic pharmaceutical of claim 1, wherein said ophthalmic pharmaceutical is in the form of eye drops.

5. The ophthalmic pharmaceutical of claim 4, wherein said concentration of polyvinylalcohol is 3–7% weight per volume.

6. The ophthalmic pharmaceutical of claim 1, wherein said ophthalmic pharmaceutical is in the form of ocular inserts.

7. The ophthalmic pharmaceutical of claim 6, wherein said concentration of polyvinylalcohol is 10–97% weight per volume.

* * * * *